US006429353B1

(12) United States Patent
Boyd et al.

(10) Patent No.: US 6,429,353 B1
(45) Date of Patent: *Aug. 6, 2002

(54) ENDOMETRIOSIS MOUSE MODEL

(75) Inventors: Jeffrey Boyd, New York, NY (US); Jerome J. Strauss, Wyndmoor; Peter Van Deerlin, Wynnewood, both of PA (US); Karen K. Yamamoto, San Clemente, CA (US)

(73) Assignees: Reprogen, Inc., Irvine, CA (US); The Trustees of the Universiy of Pennsylvania, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/047,910

(22) Filed: Mar. 25, 1998

Related U.S. Application Data

(60) Provisional application No. 60/042,542, filed on Mar. 26, 1997.

(51) Int. Cl.$^7$ .......................... A01K 67/00; C12N 15/00

(52) U.S. Cl. ............................................. 800/9; 800/21

(58) Field of Search ........................... 800/8, 9, 18, 10, 800/21; 424/93.1

(56) References Cited

U.S. PATENT DOCUMENTS

| | | | |
|---|---|---|---|
| 4,736,866 A | 4/1988 | Leder et al. | 800/1 |
| 5,434,341 A | 7/1995 | Outzen | 800/2 |
| 5,476,996 A | 12/1995 | Wilson et al. | 800/2 |
| 5,491,284 A | 2/1996 | Monosov et al. | 800/2 |
| 5,583,278 A | 12/1996 | Alt et al. | 800/2 |
| 5,650,550 A | 7/1997 | Korach et al. | 800/2 |

FOREIGN PATENT DOCUMENTS

| | | |
|---|---|---|
| EP | 0 322 240 B1 | 12/1988 |
| EP | 0 553 428 A2 | 4/1993 |

OTHER PUBLICATIONS

Cummings et al. "Effects of estrogen, progesterone and methoxychlor on surgically induced endometriosis in rats." Fundamental and Applied Toxicology, vol. 27(2): 287–290, 1995.*

Anti Cancer, Inc., "MetaMouse™: For the Development of New Effective Drugs for Cancer", *Technical Bulletin* (Jun., 1996).

"AntiCancer's now–Patented 'Meta–Mouse' Mimics Human Tumors in Organs, Not Just Under the Skin", *BioWorld Today*, (Tuesday Apr. 9, 1996).

Aoki, et al., "Successful Heterotransplantation of Human Endometrium in SCID Mice", *Obstet. Gynecol.*, 83(2):220–228 (1994).

(List continued on next page.)

*Primary Examiner*—Dave T. Nguyen
*Assistant Examiner*—Ram R. Shukla
(74) *Attorney, Agent, or Firm*—Townsend and Townsend and Crew LLP

(57) ABSTRACT

The invention provides an endometriosis mouse model wherein severely compromised immune deficient (SCID) female mice are transplanted with human xenografts of normal endometrial tissue, but result in mice with human endometriosis. Typically, the xenografts are treated with a micronized estrogen source prior to transplantation or implantation and the endogenous progesterone of the mice is eliminated also prior to transplantation of the human xenograft. These diseased mice are useful in the study of endometriosis.

10 Claims, 3 Drawing Sheets

(3 of 3 Drawing Sheet(s) Filed in Color)

OTHER PUBLICATIONS

Awward, et al., "Immunohistochemical Characterization of Human Endometrial Transplants in SCID Mice", *Abstract P–315*, p. 236 (1995) Fifty–First Annual Meeting of the American Society for Reproductive Medicine.

Bergqvist, et al., "Human Endometrium Transplanted into Nude Mice: Histologic Effects of Various Steroid Hormones", *Am. J. Pathol.*, 119(2):336–344 (1985).

Bergqvist, et al., "Human Uterine Endometrium and Endometriotic Tissue Transplanted Into Nude Mice", *Am J. Pathol.*, 121(2):337–341 (1985).

Cummings, et al., "Induction of Endometriosis in Mice: A New Model Sensitive to Estrogen", *Reprod. Toxicol.*, 9(3):233–8 (1995).

Cummings, et al., "Effect of Surgically Induced Endometriosis on Pregnancy and Effect of Pregnancy and Lactation on Endometriosis in Mice", *PSEBM*, 212:332–337 (1996).

Cummings, et al., "Promotion of Endometriosis by 2,3,7,8–Tetrachlorodibenzo–p–dioxzin in Rats and Mice: Time–Dose Dependence and Species Comparison", *Toxicol. Appl. Pharmacol.*, 138:131–139 (1996).

Dunselman, et al., "A Rabbit Model of Endometriosis", *Gynecol. Obstet. Invest.*, 27:29–33 (1989).

Dutton, "AntiCancer Inc. Scientists Identify a Key Governing Step in the Metastasis of Cancer", *Genetic Eng. News*, 16(2) (Jan. 15, 1996).

Furukawa, et al., "Orthotopic Transplantation of Histologically Intact Clinical Specimens of Stomach Cancer to Nude Mice: Correlation of Metatastic Sites in Mouse and Individual Patient Donors", *Int. J. Cancer*, 53:608–612 (1993).

Hoffman, "Orthotopic is Orthodox: Why Are Orthotopic –transplant Metatastic Models Different From All Other Models?", *J. Cell. Biochem.*, 56:1–3 (1994).

Holzman, "Of Mice and Metastasis: A New For–Profit Model Emerges", *J. Natl. Canc. Instit.*, 88(7):396–397 (1996).

Kadaba et al., "Disparate Effect of Tamoxifen in Rats with Experimentally Induced Endometriosis", *Endocrinology*, 126:3263–3267 (1990).

Kauffman, et al., "Stable Engraftment of Human Femal Genital Mucous Xenografts on SCID Mice", *Gynecol. Obstet. Invest.*, 40(2)97–100 (1998).

Kuo et al., "Liver Colonization Competence Governs Colon Cancer Metastasis", *Proc. Natl. Acad. Sci, USA*, 92:12085–12089 (1995).

Leff, "MetaMouse Models Colon Cancer Metastasis With Clinical Potential", *BioWorld Today*, 7(5):1,4 (Monday Jan. 8, 1996).

Rajkumar et al., "The Rats as an Animal Model for Endometriosis to Examine Recurrence of Ectopic Endometrial Tissue After Regressions", *Fertil. Steril.*, 53(5):921–925 (1990).

Riordan, "Patent: A Technique is Said to Ease Attachment of Tumors to Mice, Making Them 'Little Cancer Patients'", *The New York Times*, (Monday Mar. 4, 1996).

Rock et al., "Intraocular Endometrium in the Rabbitt as a Model for Endometriosis", *Fertil Steril.*, 59(1):232–235 (1993).

Shrine, "Batimastat Reduces Metastases", *BioWorld Today*, (Friday, Mar. 25, 1995).

Sillem et al., "Ectopic Growth of Endometrium Depends on its Structural and Proteolytic Activity in the Cynomolgus Monkey (*Macacca fasciculari*) model of endometriosis", *Fertil. Steril.*, 66(3)468–473 (1996).

Togo et al., "Host Organ Specifically Determines Cancer Progression", *Cancer Res.*, 55:681–684 (1995).

Wang et al., "Matrix Metalloproteinase Inhibitor BB–94 (Batimastat) Inhibits Human Colon Tumor Growth and Spread in a Patient–like Orthotopic Model in Nude Mice", *Cancer Res.*, 54:4726–4728 (1994).

Zamah, et al., "Transplantation of Normal and Ectopic Human Endometrial Tissue into Athymic Nude Mice", *Am. J. Obstet. Gynecol.*, 149(6):591–597 (1984).

* cited by examiner

ENDOMETRIOSIS MOUSE MODEL

This application claims priority to U.S. Provisional Application No. 60/042,542 filed Mar. 26, 1997, the disclosure of which is hereby incorporated by reference in its entirety.

BACKGROUND OF THE INVENTION

This invention relates to an endometriosis mouse model wherein severely compromised immune deficient (SCID) female mice are transplanted with human xenografts of normal endometrial tissue, but result in mice with human endometriosis tissue. These diseased mice are useful in the study of endometriosis, in particular to identify nucleic acid sequences or amino acid sequences that up- or down-regulate the diseased state, or that are endometriosis specific.

Endometriosis is a disease affecting women of reproductive age, causing substantial debilitation, such as pelvic pain, and possible sterility or infertility, depending upon the severity of the condition. Most experts agree that endometriosis originates from retrograde menstruation of normal endometrial fragments that then implant on to peritoneal surfaces, from vascular or lymphatic dissemination of endometriosis lesions to other parts of the body, and/or from metaplasia, i.e., the abnormal transformation of one differentiated tissue into another. *Modem Approaches to Endometriosis.*, eds. E. Thomas and J. Rocky, Kluwer Academic Publishers Boston (1991).

Typically, diagnosing endometriosis requires an invasive procedure, which results in the possibility of infection and other disadvantages associated with surgery. At present, the most effective therapy for treatment of endometriosis is surgical intervention, along with the administration of growth factor antagonists; ovarian suppression treatments, such as gonadotropin-releasing hormone (GnRH) agonists; and immunomodulators to inhibit the implantation of endometrial cells into undesired tissues. Therefore, it is desirable to develop procedures, techniques, and treatments that are easier to use and are more effective in the diagnosis and/or treatment of the disease.

One approach in general disease diagnosis has been to develop animal models that mimic certain disease states, and thereby study the indications of the disease and also study the impact of proposed treatment regimes. Primates are the only animal class to spontaneously develop endometriosis, although it is mainly a human disease condition. However, the use of non-human primates to study this disease is very expensive and labor-intensive due to the care required for the animals. Also, primates have a longer reproductive cycle than other laboratory animals, making a primate model less desirable as a system for preliminary endometriosis studies.

Human xenografts of normal endometrial tissue or endometriosis tissue have been transplanted into nude mice to create certain mouse models. See Zamah, et al., Transplantation of Normal and Ectopic Human Endometrial Tissue into Athymic Nude Mice , *Am. J. Obstet. Gynecol.*, 149:591–597 (1984); Berqvist, et al., Human Uterine Endometrium and Endometriosis Tissue Transplanted into Nude Mice , *Am. J. Pathol.*, 121:337–341 (1985); and Berqvist, et al., Human Endometrium Transplanted into Nude Mice , *Am. J. Pathol.*, 119:336–344 (1985). More recently, SCID mice have been transplanted subcutaneously or intraperitoneally with normal human endometrium. See Aoki, et al., Successful Heterotransplantation of Human Endometrium in SCID Mice, *Obstet.Gynecol.*, 83:220–228 (1994); and Awwad, et al., Immunohistochemical Characterization of Human Endometrial Transplants in SCID Mice Abstract P-315, page 236 (1995) presented at the Fifty-First Annual Meeting of the American Society for Reproductive Medicine.

A particular mouse model of surgically-induced endometriosis was evaluated to determine the effects of pregnancy on endometriosis and the effects of endometriosis on pregnancy. However, chopped mouse uterine tissue was utilized. See Cummings, et al., Effect of Surgically Induced Endometriosis on Pregnancy and Effect of Pregnancy and Lactation on Endometriosis in Mice , Endometriosis and Pregnancy in Mice, *PSEBM,* 212:332–337 (1996). The promotion of endometriosis using TCDD was discussed in Cummings, et al., Promotion of Endometriosis by 2,3,7,8-Tetrachlorodibenzo-p-dioxin in Rats and Mice: Time-Dose Dependence and Species Comparison, *Toxicol. Appl. Pharmacol.*, 138:131–139 (1996).

However, the existing models result in the perpetuation and proliferation of the implanted material in its original form rather than exhibiting the progression of normal endometrial tissue to endometriosis diseased tissue, nor do these models indicate the progression of human tissue. Due to the relevance of the disease's pathology, it is important to have a model system which mimics the development of the human disease state.

SUMMARY OF THE INVENTION

One aspect of the invention provides a novel mouse model for human endometriosis wherein normal human endometrial tissue grows and mimics the progression to human endometriosis. The endometriosis mouse model is prepared or generated by a method which comprises a. eliminating endogenous progesterone from a severely compromised immune deficient (SCID) female mouse;

b. adding a micronized exogenous estrogen source to a xenograft of human normal endometrial tissue;

c. implanting the xenograft into the intraperitoneal cavity of the mouse;

d. adding an exogenous estrogen source to the mouse before and after implantation of the xenograft; and e. allowing the xenograft to grow and mimic the progression of human endometriosis tissue. The length of time for progression is typically 3 to 7 weeks, preferably about 5 weeks.

Another preferred aspect of the invention is a female SCID mouse model for endometriosis, wherein said mouse is characterized by having a xenograft of human normal endometrical tissue implanted into the mouse's intraperitoneal cavity and wherein the tissue is allowed to grow and progress to endometriosis.

Usually the endogenous progesterone is eliminated from the SCID mouse by a bilateral oophorectomy or by administration of an anti-progesterone agent. The mouse selected for the model is a female mouse in which her immune system is severely compromised, so that the implanted xenograft will be accepted, grow and develop.

In preparing the xenograft, a section of human normal endometrial tissue is identified, isolated from its human donor, and fragmented, and then an exogenous source of estrogen is added. Typically, this estrogen is micronized and is in water-soluble form prior to its administration or addition to the xenograft.

The prepared xenograft is implanted or transplanted into the intraperitoneal cavity of the mouse and exogenous estrogen is administered to the mouse both before and after implantation. The xenograft then grows and develops in the mouse, mimicking the progression of human endometriosis. Approximately from about 0.05 to about 1.5 cubic centimeters (cc) of the solid tissue is isolated with the xenograft optionally suspended in a physiologically-compatible solution or nutrient medium and the suspension injected into each mouse at an amount from about 0.4 cc to about 0.6, cc so that the mouse receives about 0.2 cc of material. Also, an antibiotic can be administered to the mouse in conjunction with the xenograft implantation.

The source of the xenograft tissue is from a human female; usually the result of a hysterectomy or an endometrial biopsy. Preferably, the xenograft is obtained from a pre-menopausal female not previously treated with gonadotropin-releasing hormone (GnRH) agonists.

Various sources of exogenous estrogen can be used, such as beta-estradiol-17-cypionate, poly-estradiol phosphate, beta-estradiol benzoate, and the like, and is administered to the xenograft and the mouse in different dosages and methods. The estrogen is added to the xenograft in a water-soluble or micronized form to reach a concentration from about 50 to about 500 nanomolars (nM); whereas the mouse receives from about 60 micrograms (ug) per kilogram (kg) per week to about 120 ug per kg per week of exogenous estrogen. The estrogen is administered intramuscularly or subcutaneously to the mouse starting at least one day prior to the implantation of the xenograft and continuing once a week after implantation.

This invention also provides molecular and immunohistochemical/immunopathological profiles in the mouse which are identical to human endometriosis, thus generating a model system to mimic the progression of normal endometrial tissue to diseased endometriosis tissue. Using the model, one of skill can screen and evaluate various potential therapies or prophylactics for treating or preventing endometriosis, since the model replicates the human clinical condition and provides clinical responses as an in vivo system. Further, the model provides a means to evaluate the effect of dosages, schedules, delivery systems, and routes of administration, as well as to identify nucleic acids or amino acids associated with the disease.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

DESCRIPTION OF THE PREFERRED EMBODIMENT

Figure 1:
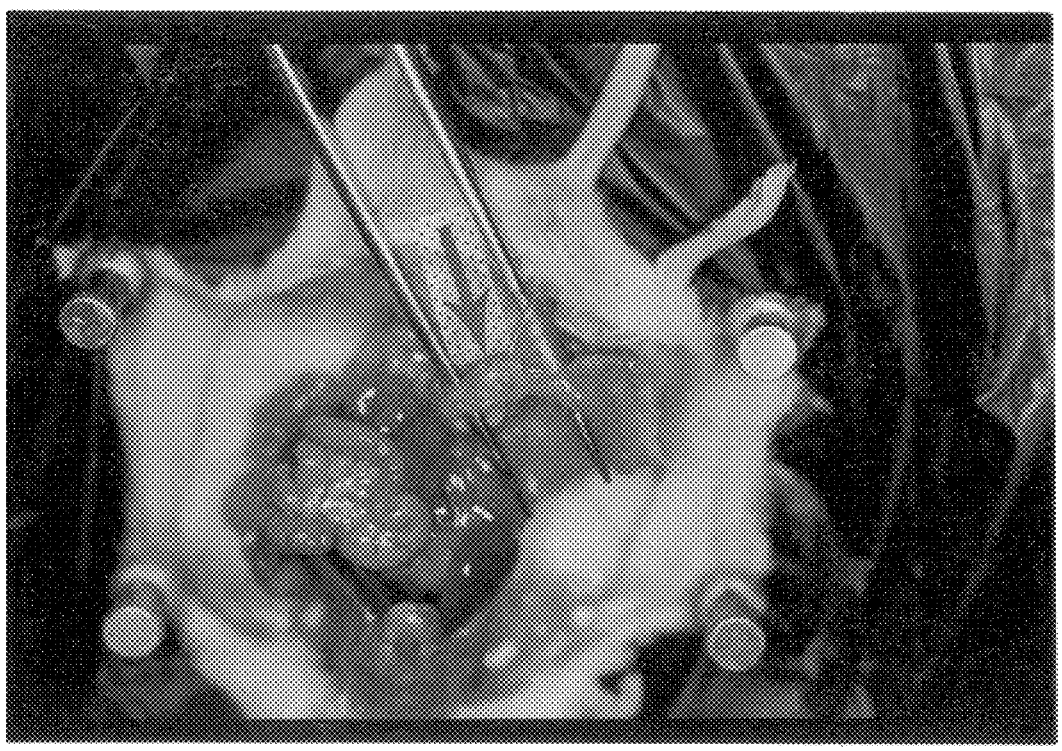
FIG. 1 shows a gross view of mouse peritoneal cavity demonstrating endometriosis implant (arrow).

The present invention provides a novel mouse model for human endometriosis wherein normal human endometrial tissue grows and mimics the progression to human endometriosis. The mouse model is prepared or generated by the method generally described above and specifically herein.

Endometriosis is a female disease in which endometrial tissue is found outside the uterus, its normal anatomic location, and it affects women of reproductive age, causing substantial debilitation and possible sterility or infertility, depending upon the severity of the condition. Endometriosis is prevalent in 1-2% of the general female population. Endometrial tissue is improperly implanted in other anatomical sites, such as the peritoneal cavity, kidneys, and more often the ovaries. See Taylor, et al., *Brit. J. Ob & Gyn.,* 98:680–684 (1991); and Vigano, et al., Fertility and Sterility, 56:894 (1991); Badaway, et al., *Fertility and Sterility,* 53:930 (1990).

Clinical signs and symptoms usually consist of severe dysmenorrhea, dyspareunia and pelvic pain due to intrapelvic bleeding and periuterine adhesions. Nodules with a red-blue to yellow-brown appearance are found on or just beneath the surfaces of the site of involvement. Extensive fibrous adhesions can be found among the reproductive structures, such as the ovaries. The disease is histologically diagnosed if two of the three following features are identified outside the uterine cavity: endometrial glands, stroma and hemosiderin pigment. See Robbins, *Pathologic Basis of Disease 5th Edition,* W. B. Saunders Company, Philadelphia (1994).

Currently, laparoscopy is the procedure of choice for the diagnosis of endometriosis, because it enables the surgeon to possibly evaluate the extent of the disease. Other modalities for evaluation of suspected endometriosis include measurement of serum cancer antigen 125 (CA 125) and imaging studies, such as ultrasound and magnetic resonance imaging. However, these diagnostic tools have their limitations, since they do not allow for distinguishing endometriosis over other physiological situations, such as benign pelvic or ovarian conditions.

For the mouse model system of the invention, a severely compromised immune deficient mouse, also known as severe combined immunodeficiency, (SCID) mouse is selected. The SCID mouse is congenitally deficient in T- and B-lymphocyte function and has no natural killer lymphocyte activity and, as a result, receives heterotransplant or xenograft tissue more readily without the rejection of the transplant or xenograft. See Bosma, et al. The SCID mouse mutant: Definition, characterization, and potential uses , *Ann. Rev. Immunol.,* 2:323–350 (1993). Human heterotransplants are adversely affected by other immunological reactions and therefore, the desired model must minimize or eliminate these effects. The SCID mouse is preferred over other mouse types, such as the nude mouse due to the SCID mouse's more compromised immune system.

A homozygous nude mouse (nu/nu) lacks the defensive T-lymphocyte system as a consequence of congenital thymus aplasia, i.e., is athymic, but has comensatory high natural killer lymphocyte activity, which is considered to contribute to the rejection or suppression of heterotransplants or xenografts. The recessive mutation nude in mice, which in homozygous form causes hairlessness, is also associated with failure to develop T cells from bone marrow progenitors. See Janeway and Travers, *Immunobiology,* Current Biology Ltd. 1994.

SCID mice can be produced by homologous recombination via transgenesis or gene knock-out techniques, or can be obtained commercially. For example, homozygous CB 17 strain SCID mice (scid/scid) are available from Taconic Labs (Germantown, N.Y.) and preferrably Charles River Labs (Wilmington, Mass.).

Since the disease of interest is endometriosis, a female mouse is selected, so that the progression of the disease can be properly assessed. Typically, a mature female mouse is selected, i.e., one that is capable of reproduction.

Once the SCID mouse is selected or identified, the endogenous progesterone is eliminated from the mouse, since the hormone may interfere with or inhibit endometrial proliferation. The preferred elimination method is via bilateral oophorectomy or ovariectomy, wherein the mouse's ovaries are surgically removed and/or clipped or ligated away. See *Handbook on the Laboratory Mouse*, ed. Charles Crispens, Jr., Thomas Publishers, Springfield, Ill. (1975), page 40. The use of an oophorectomy also minimizes the importance of timing the implantation with the estrous cycle of the mouse.

Alternatively, the effect of the endogenous progesterone can be eliminated or minimized by the administration of an anti-progesterone agent or drug, such as mifepristone and the like. See Baird, et al. *Human Reproduction*, 10:2270 (1995).

To prepare the human xenograft tissue for implantation or transplantation, a human female donor must be identified and then the appropriate normal endometrial tissue removed. The human endometrial tissue can be obtained by any method, but preferably it is obtained surgically from a hysterectomy specimen or from a endometrial biopsy specimen. (If the specimen utilized is from a biopsy, it is preferably obtained in the luteal phase of the menstrual cycle.) The donor is usually a pre-menopausal woman who has not been previously treated with hormones or hormone-responsive drugs. For example, the xenograft can be isolated from a female who has not been given gonadotropin-releasing hormone (GnRH) agonists, also known as Luteinizing Hormone Releasing Hormone (LHRH) agonists.

To the extent possible, the specimen should contain only normal endometrial tissue and not be contaminated by surrounding tissue or inflammatory, immuno-regulatory cell type tissue. Normal endometrial tissue lines the uterine cavity. The histology of normal endometrium is characterized by simple columnar ciliated epithelium supported by a highly cellular connective tissue stroma containing many simple tubular glands. See *Histology—A Text and Atlas*, eds. M. Ross and E. Reith, Harper and Row Publishers, New York (1985) and *Blaustein's Pathology of the Female Genital Tract. Third Edition*, ed. R. J. Kurman, Springer—Verlag, New York (1987).

Approximately 0.05 cc to about 1.5 cc of human tissue is selected for implantation. The preferred amount is about 0.05 cc to about 0.2 cc.

After the xenograft tissue is isolated, it is prepared for transplantation or implantation into the SCID mouse. The xenograft is fragmented for administration by any mechanical means, such as teasing the tissue to the appropriate size with forceps, mechanically mincing the tissue, and the like, so long as the fragmentation is performed under sterile conditions. Although the xenograft or heterotransplant can be implanted in various amounts and in certain sizes, it is preferable to prepare material so that it can easily pass through a 20-gauge needle and can be injected into the intraperitoneal cavity of the mouse.

The peritoneum of the mouse is a serous sac, consisting of mesothelium and a thin layer of irregular connective tissue, that lines the abdominal cavity and covers most of the viscera contained therein. See *Stedman's Pocket Medical Dictionary*, Williams & Wilkins, Baltimore (1987). The xenograft is injected into the cavity under sterile conditions. Optionally, the mouse can be anesthetized using a suitable anesthetic.

Prior to injection, the fragmented xenograft is treated with a micronized or water-soluble form of estrogen, such as estradiol cypionate and the like, although the micronized estrogen can be added prior to fragmentation. The estrogen source is micronized, before administration to the xenograft in an amount from about 50 to about 500 nanomolars (nM), preferably about 100 nM. (Micronization is the process of making an oil-soluble hormone water soluble.) The administration of a micronized estrogen source to the xenograft increases the take rate of the implant, i.e., the successful transplantation of the xenograft such that it remains in the mouse and grows, and such that it is still present at the time of the mouse necropsy.

The xenograft is typically suspended in a physiologically-compatible solution or nutrient medium, such as Dulbecco's modified eagle medium (DMEM) or phosphate buffered saline (PBS) and the like prior to implantation and about 0.4 cc to about 0.6 cc of the suspension is administered to each mouse. The preferred suspension amount is 0.5 cc. Optionally, an antibiotic is added to the suspension to minimize infection, using such antibiotics such as streptomycin, penicillin, and the like. Applicable antibiotics and suspension solutions are described in *Remington's Pharmaceutical Sciences*. 19th Ed., Mack Publishing Company, Easton, Pa. (1995). Ideally, the xenograft tissue is fresh tissue, i.e., less than two hours after harvesting, but can be frozen and then thawed.

The SCID mouse is also treated with an estrogen source prior to implantation and thereafter. The estrogen source is administered intramuscularly or subcutaneously starting at least one day prior to the xenograft's implantation and continuing once a week afterwards until the mouse is sacrificed and the human endometriosis tissue isolated. The mouse typically receives from about 60 micrograms (ug) per kilogram (kg) per week to about 120 ug/kg/week. The source of estrogen can be any substance, natural or synthetic, that exerts the biological effects characteristic of estrogenic hormones formed by the ovary, and includes beta-estradiol-17-cypionate, poly-estradiol phosphate, beta-estradiol benzoate, and the like.

The xenograft is allowed to grow and mimic the progression to human endometriosis tissue. The development of endometriosis is determined by histology as described above. The progression to endometriosis is determined by increased observation of adhesion formation and the incidence of lesions with cystic components. The optimal treatment is based on a 100% "take rate" which includes the development of adhesions. Adhesions are an indication beyond transplantation, in that the body is making adhesions to the lesions as part of an inflammatory process. Additionally, the development of the cystic component indicates a progression to functioning tissue in that the endometrium has a secretory function and functioning glands are developed. The fact that these activities are occurring outside the natural environment is definitive of disease (ectopic vs. eutopic). Typically, the progression should occur between three to seven weeks after implantation, usually about five weeks. Of course, the mice can be allowed to continue beyond seven weeks depending upon the particular analysis and use of the mice.

This invention also provides molecular and immunohistochemical or immunopathological profiles in the mouse that are identical to human endometriosis and provides endometriosis tissue uncontaminated by human other tissues. Therefore, this mouse model mimics the progression of normal human endometrial tissue to diseased human endometriosis tissue. Using this in vivo model, one can screen and evaluate various potential therapies or other modalities for their effectiveness in treating or alleviating endometriosis, and evaluate any potential prophylatics.

Since the model is an in vivo system it replicates, or is analogous to, the human clinical condition and provides clinical responses. Further, the model provides a means to evaluate the effect of dosages, schedules, delivery systems, drug sensitivities, and routes of administration for any effective endometriosis treatment.

The model also can be utilized to identify nucleic acid sequences, ie, genes, and/or amino acid sequences, i.e., proteins, that are associated with endometriosis and its development, especially those that up- or down-regulate the disease.

In addition to these uses, the mouse model can act as a surrogate patient to evaluate the impact of a selected drug on the endometriosis tissue before actual administration to the patient having the disease, and further, can aid in the prognosis of a patient.

EXAMPLES

The following examples are for illustration only and are not intended to limit the invention in any way.

Human Endometrium

Human endometrium from pre-menopausal women was obtained either from residual endometrial biopsy material (protocol Group I) during the luteal phase of the menstrual cycle of patients undergoing an infertility work-up (N=7), or from fresh hysterectomy specimens (for myomatous uterus) (N=14) (protocol Groups II and III). The endometrial tissue from the hysterectomy specimens was gently scraped from the myometrium with a sterile scalpel blade and placed into a Dulbecco's modified eagle medium (DMEM), low glucose, L-glutamine solution (BRL/GIBCO (Life Technologies) Cat. #11885–084), which was supplemented with penicillin and streptomycin.

The tissue was mechanically minced, under sterile conditions, until it could pass easily through a 20-gauge needle. The volume of the minced tissue pellet ranged from 0.1 to 1.0 cc, and the aliquots were suspended in 0.5 cc of DMEM. Micronized water-soluble estradiol in distilled water was added to the samples in Group III to reach a final concentration of 100 nM. The 0.5 cc tissue suspension was then injected into the peritoneal cavity of the mice with a 20-gauge needle under sterile conditions.

The material from the endometrial biopsies was collected by pipelle biopsy in the midluteal phase of the menstrual cycle. Three centimeters (cm) of the tissue were sent to pathology for endometrial dating assessment, while the residual tissue (at least 2 cm in length) was placed in DMEM and prepared in the same manner as described above.

SCID Mice

Female CB 17 strain SCID mice (Taconic Labs), age 4–12 weeks, were housed in a germ-free environment and pre-treated with long-acting subcutaneous (0.05 cc) estradiol cypionate in cottonseed oil at a dose of 2.5 ug per mouse every week (approximately 60.0 ug/kilograms (kg)/week). The mice in protocol Group III were oopharectomized several weeks prior to xenograft treatment to prevent endogenous progesterone production, which production might inhibit endometrial proliferation. The Group III mice also received a four-fold increase in estradiol cypionate.

After the implantation of the human endometrium, the weekly dosing of estrogen continued for all groups until the mice from all groups were sacrificed about 3–7 weeks, averaging about 5 weeks, by carbon dioxide asphyxiation on the day following the last estradiol injection. At necropsy, the peritoneal cavity was inspected closely for any adhesions or lesions suspected of endometriosis. These lesions were resected and a representative portion was fixed in 95 % ethanol.

Pathology Processing

Paraffin blocks were made from the fixed tissue, sliced, and then stained with hematoxylin and eosin before the samples were placed on slides. The prepared slides were reviewed by at least two independent pathologists. Endometriosis was considered present when epithelial glands were found in the presence of stromal tissue characteristic of endometriosis.

Results

All but two of the mice survived until the planned sacrifice date. The two mice (Group II) were injected with tissue from the same patient and both expired four days after the implantation without an obvious etiology. No gross lesions were found during the autopsy on these two mice.

As shown in Table 1, three different protocols were used in the studies and the successful implantation take rate improved with each successive group.

TABLE 1

Description and Results from Three Different Protocols

| Group | Tissue Source | E2 Dose | Mice/Patient | Implantation Rate (%) |
| --- | --- | --- | --- | --- |
| Group I | EM biopsy | 30 mcg/kg | 2 | 5/14 (36%) |
| Group II | hysterectomy | 30 mcg/kg | 2–3 | 8/16 (50%) |
| Group III | hysterectomy | 120 mcg/kg | 1 | 6/6 (100%) |

A visual inspection of the gross lesions indicated that they were about 2 to about 10 millimeters (mm) in size, pale pink to brown, and occasionally consisted of a chocolate cyst. (The ovaries become markedly distorted by large cystic spaces filled with brown blood debris.) These lesions were most commonly located on the anterior peritoneal surface in the pelvic fat pad surrounding the uterus. Often they were involved with adhesions to the bowel or the spleen.

Histologically, the lesions that were diagnosed as human endometriosis were very characteristic of the common spontaneous human endometriosis lesions seen during human pathology.

FIG. 1 shows a gross view of mouse peritoneal cavity demonstrating endometriosis implant (arrow).

Figure 2:
FIG. 2 is a histological preparation of an endometriosis implant on the intestine. The human endometriosis implant contains both glandular epithelium and stroma (X400).

FIG. 2 is a histological preparation of an endometriosis implant on the intestine. The human endometriosis implant contains both glandular epithelium and stroma (X400).

Figure 3:
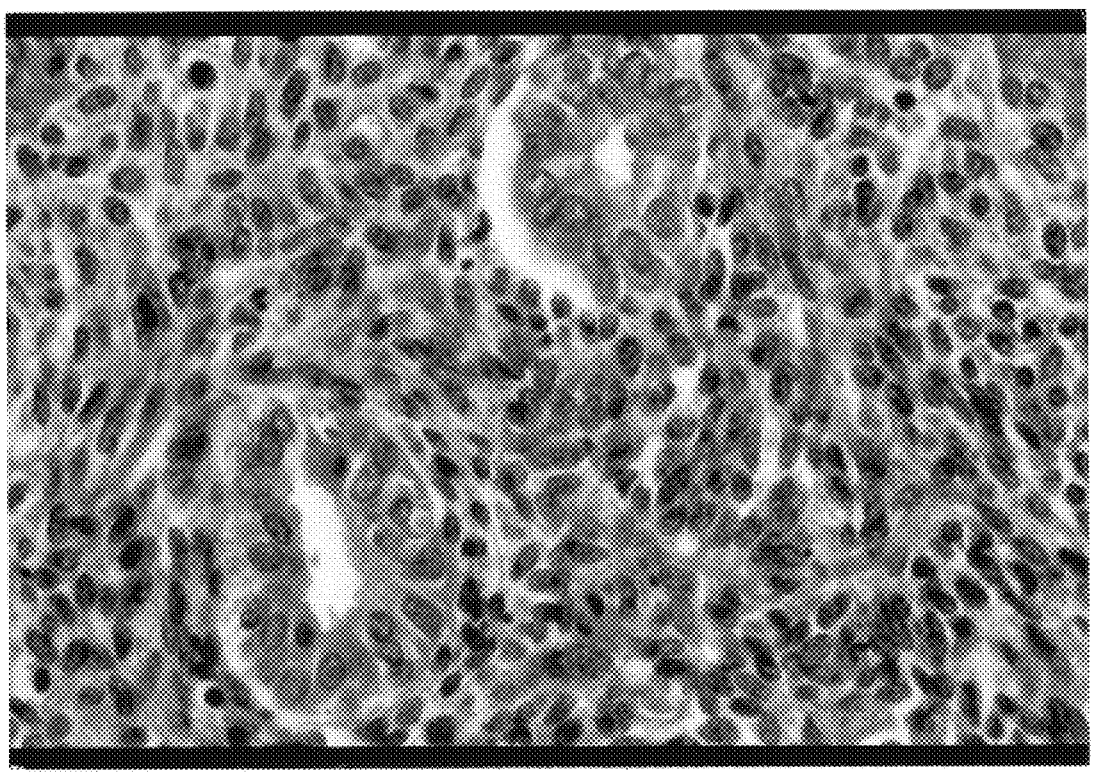
FIG. 3 is a high power view of endometriosis implant showing stroma, glands and a deposit of hemosiderin (X1000).

FIG. 3 is a high power view of endometriosis implant showing stroma, glands and a deposit of hemosiderin (X1000).

All references and patent documents cited herein are incorporated by reference in their entireties and for all purposes to the same extent as if each individual reference or patent document was specifically and individually indicated to be incorporated by reference.

Many modifications and variations of this invention can be made without departing from its spirit and scope, as is apparent to those skilled in the art. The specific embodiments described herein are offered by way of example only, and the invention is to be considered in light of the claims, as well as the full scope of equivalents to which such claims are entitled.

What is claimed is:

1. A method for generating a mouse model for human endometriosis comprising:
   a. eliminating endogenous progesterone from a severely compromised immune deficient (SCID) female mouse by a bilateral oophorectomy or by administration of an anti-progesterone agent;
   b. adding a micronized exogenous estrogen source to a xenograft of human normal endometrial tissue;

c. implanting the xenograft into the intraperitoneal cavity of the mouse;

d. adding an exogenous estrogen source to the mouse before and after implantation of the xenograft; and e. allowing the xenograft to grow and nimic the progression of human endometriosis tissue;

wherein the oophorectomy or administration of the anti-progesterone agent is performed at least one week prior to the implanting of the xenograft into the intraperitoneal cavity of the mouse.

2. The method of claim 1 wherein the micronized exogenous estrogen source of step b and the exogenous estrogen source of step d are selected from the group consisting of beta-estradiol-17-cypionate, poly-estradiol phosphate, and beta-estradiol benzoate; and wherein the micronized exogenous source of step b is added to the xenograft in an amount from about 50 to about 500 nanomolars (nM); and wherein the exogenous estrogen source of step d is added to the mouse in an amount from about 60 micrograms (ug) per kilogram (kg) per week to about 120 ug per kg per week.

3. The method of claim 2 wherein the exogenous estrogen source of step d is added to the mouse via intramuscular or subcutaneous administration starting at least one day prior to the implantation of the xenograft and continuing once a week after implantation.

4. The method of claim 3 wherein the xenograft is implanted via injection into the mouse in an amount from about 0.05 to about 0.2 cubic centimeters (cc).

5. The method of claim 4 wherein the xenograft is obtained from a human female hysterectomy specimen or from a human female endometrial biopsy specimen.

6. The method of claim 5 wherein the xenograft is obtained from a pre menopausal human female not previously treated with gonadotropin-releasing hormone (GnRH) agonists.

7. The method of claim 1 wherein the xenograft is suspended in a physiologically-compatible solution or nutrient medium.

8. The method of claim 7 wherein the solution or medium is Dulbecco's modified eagle medium (DMEM) or phosphate buffered saline (PBS).

9. The method of claim 1 wherein an antibiotic is administered to the mouse in conjunction with the implantation of the xenograft.

10. A female SCID mouse model for human endometriosis, wherein said mouse model is produced by the method of claim 1 and wherein said mouse model is characterized by having a xenograft of human normal endometrial tissue implanted into the mouse's intraperitoneal cavity and wherein the tissue is allowed to grow and progress to endometriosis.

* * * * *